US006904649B2

(12) United States Patent
VanBenschoten et al.

(10) Patent No.: US 6,904,649 B2
(45) Date of Patent: Jun. 14, 2005

(54) DIRECT HOOK ENGAGEMENT

(75) Inventors: Brian J. VanBenschoten, Rochester, NH (US); Christopher M. Gallant, Nottingham, NH (US); Hariani Zaki Sepanik, Bedford, NH (US); Heidi S. Tremblay, Windham, NH (US)

(73) Assignee: Velcro Industries B.V., Curacao (NL)

( * ) Notice: Subject to any disclaimer, the term of this patent is extended or adjusted under 35 U.S.C. 154(b) by 15 days.

(21) Appl. No.: 10/169,889

(22) PCT Filed: Jan. 30, 2002

(86) PCT No.: PCT/US02/02570

§ 371 (c)(1), (2), (4) Date: Nov. 4, 2002

(87) PCT Pub. No.: WO02/060294

PCT Pub. Date: Aug. 8, 2002

(65) Prior Publication Data

US 2003/0121128 A1 Jul. 3, 2003

Related U.S. Application Data

(60) Provisional application No. 60/265,258, filed on Jan. 31, 2001.

(51) Int. Cl.$^7$ .......................... A44B 18/00; A61F 13/15
(52) U.S. Cl. ............................. 24/452; 24/442; 24/306; 2/912; 2/920; 604/391
(58) Field of Search .......................... 24/306, 442–452; 428/100; 2/912; 604/391

(56) References Cited

U.S. PATENT DOCUMENTS

| | | | |
|---|---|---|---|
| 3,009,235 A | 11/1961 | DeMestral | |
| 3,031,730 A | 5/1962 | Morin | |
| 3,083,737 A | 4/1963 | DeMestral | |
| 3,138,841 A | 6/1964 | Naimer | |
| 3,147,528 A | 9/1964 | Erb | |
| 3,154,837 A | 11/1964 | DeMestral | |
| 3,312,583 A | 4/1967 | Rochlis | |
| 3,708,833 A | 1/1973 | Ribich et al. | |
| 3,762,000 A | 10/1973 | Menzin et al. | |
| 3,770,359 A | 11/1973 | Hamano | |
| 3,913,183 A | 10/1975 | Brumlik | |
| 3,964,482 A | 6/1976 | Gerstel et al. | |
| 4,024,003 A | 5/1977 | Buhler | |

(Continued)

FOREIGN PATENT DOCUMENTS

| | | |
|---|---|---|
| EP | 0 497 620 | 8/1992 |
| WO | WO 98/11937 | 3/1998 |
| WO | WO99/11452 | 3/1999 |
| WO | WO 00/73063 | 12/2000 |

OTHER PUBLICATIONS

PCT International Search Report mailed May 29, 2002 for International Application No. PCT/US02/02570 (five pages).

Han et al., "Micromechanical Velcro", Journal of Micro-Electromechanical System, vol. 1, No. 1, pp. 39–43, Mar. 1992.

Microneedles, Breakthroughs in Science, Technology and Medicine, Discover, Oct. 22, 1998 (two pages).

*Primary Examiner*—Robert J. Sandy
(74) *Attorney, Agent, or Firm*—Fish & Richardson, P.C.

(57) ABSTRACT

A fastening tape has a sheet-form base carrying an array of hooking members (10,22,24,34) each having a height (h) of about 0.008 inch (0.2 millimeter) or less, as measured from the base, and fiber-engaging features, such as re-entrant tips (18,32), disposed less than about 0.003 inch (0.08 millimeter) from their upper surfaces, as measured normal to the base. Such hooking members are employed to releasably engage directly into foams and fine denier non-woven materials, such as those of insulation, filters, construction moisture barriers, disposable gowns and diapers.

65 Claims, 3 Drawing Sheets

U.S. PATENT DOCUMENTS

| | | |
|---|---|---|
| 4,133,307 A | 1/1979 | Ness |
| 4,290,832 A | 9/1981 | Kalleberg |
| 4,794,028 A | 12/1988 | Fischer |
| 4,894,060 A | 1/1990 | Nestegard |
| 4,963,140 A | 10/1990 | Robertson et al. |
| 4,984,339 A | 1/1991 | Provost et al. |
| 5,058,247 A | 10/1991 | Thomas et al. |
| 5,067,210 A | 11/1991 | Kayaki |
| 5,279,604 A | 1/1994 | Robertson et al. |
| 5,312,456 A | 5/1994 | Reed et al. |
| 5,315,740 A | 5/1994 | Provost |
| 5,551,130 A | 9/1996 | Tominaga et al. |
| 5,604,963 A | 2/1997 | Akeno |
| 5,692,271 A | 12/1997 | Provost et al. |
| 5,781,969 A | 7/1998 | Akeno et al. |
| 5,875,527 A | 3/1999 | Lacey et al. |
| 5,900,350 A | 5/1999 | Provost et al. |
| 5,945,193 A | 8/1999 | Pollard et al. |
| 5,953,797 A | 9/1999 | Provost et al. |
| 5,997,522 A | 12/1999 | Provost et al. |
| 6,163,939 A | 12/2000 | Lacey et al. |
| 6,209,177 B1 | 4/2001 | Murasaki |
| 6,329,016 B1 | 12/2001 | Shepard et al. |

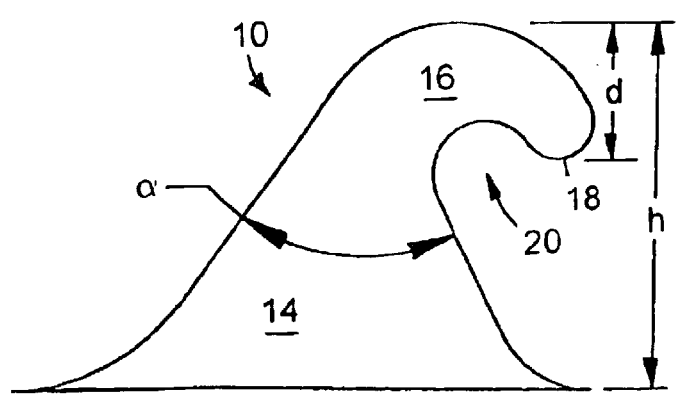
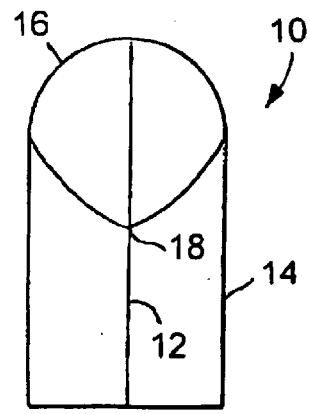
FIG. 1          FIG. 1A
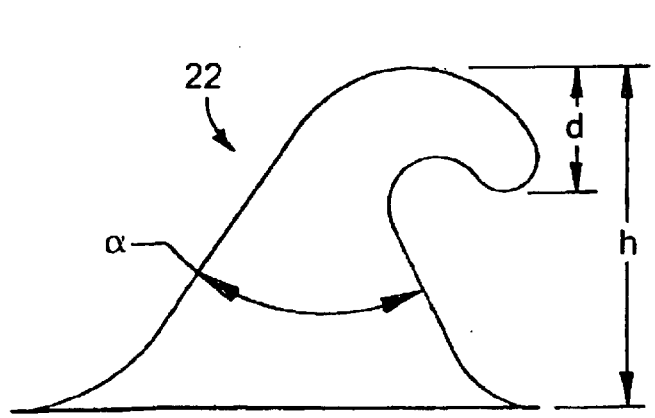
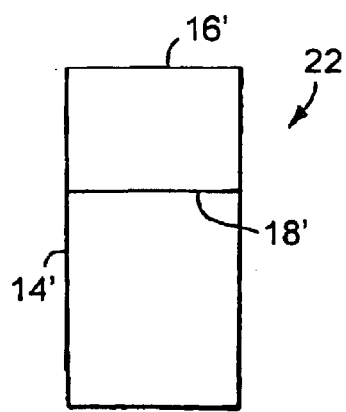
FIG. 2          FIG. 2A

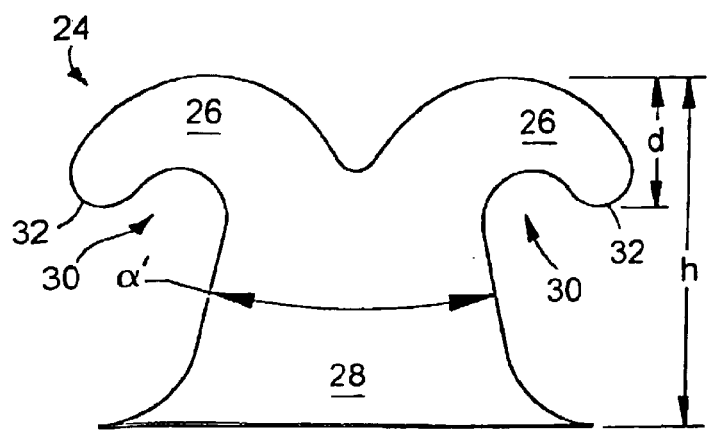
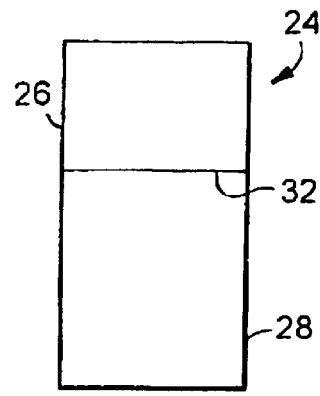
FIG. 3          FIG. 3A
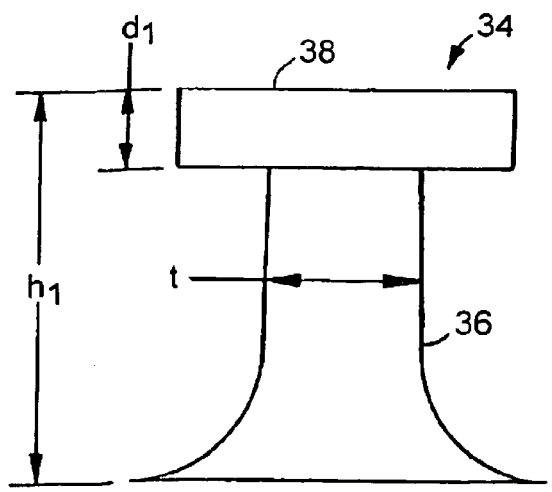
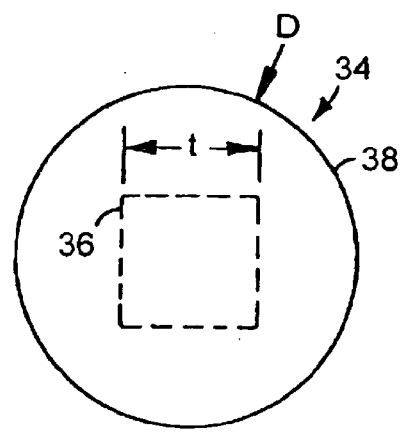
FIG. 4          FIG. 4A

DIRECT HOOK ENGAGEMENT

This is a 371 of International Patent Application No. PCT/US02/02570, with an international filing date of Jan. 30, 2002 which claims the benefit of Provisional Application No. 60/265,258, filed Jan. 3, 2001.

TECHNICAL FIELD

This invention relates to hook and loop fastening, and more particularly to male hook members adapted to engage a penetrable surface to form a releasable closure.

BACKGROUND

Plastic hook tape can be produced in a continuous molding process described by Fischer in U.S. Pat. No. 4,794,028, hereby incorporated by reference. Such hook tapes have small hook members integrally molded to extend from a broad side of a sheet form base, and each hook member generally has a head portion overhanging the base to form an engageable crook in at least one direction along the longitudinal molding direction of the hook tape. Mushroom-type hook fasteners may be formed by molding stems in a Fischer-type continuous molding process, and then flattening the ends of the molded stems to form heads overhanging the base in generally all directions.

Traditionally, a male fastener tape will be provided with an array of many such hook members and arranged to engage a mating loop product or other female fastener member, to form a releasable closure by what has come to be known as hook and loop fastening. Discrete sections of hook and loop fastener tape may be sewn as specifically located patches onto a garment, for example.

SUMMARY

We have developed hooking members of a size and shape suitable for releasable engagement directly with many materials commonly employed in many products for reasons completely unrelated to hook fastening, effectively enabling such products to be provided with cost-effective, releasable fastening means without the need of a separate hook-engageable (e.g., loop) member.

Examples of the common materials into which our hooks can directly engage include non-woven materials employed in inexpensive medical gowns and other garments, non-woven polypropylene construction barrier materials, and some open cell foams in common use as padding and filter materials.

Because no separate loop patch need be added to the product, the fastening is provided with substantial ease of use, as the hooking member can be engaged directly into any exposed portion of the product comprised of the engageable material. This can enable a garment to be readily fitted to many user sizes, and donned and removed rapidly. Garment closures incorporating these hooks can also be engaged anywhere on the garment after use, for holding the garment in a wrapped, compact condition. This can be particularly useful for storage, or for disposal after garment contamination, for example.

Our invention results in part from our realization that many applications do not require substantial closure holding forces, and that low peel and shear strengths have some useful advantage over stronger fastenings in some applications.

In some preferred embodiments, the invention features hooking members of molded form, having a molded head portion that overhangs the base of the fastener to form a crook for engaging a discrete feature of the mating fastening material. In some cases, the hooking member is a J-shaped hook overhanging the base in a single direction, and in other cases it is of palm-tree shape, overhanging the base in two opposite directions.

In another preferred embodiment, the invention features particularly small mushroom-type hooking members, preferably with molded stems and head portions that overhang the stems in multiple directions. Preferably, the head portions are formed by rapidly heating the ends of the molded stems, such as by open flame, and then quickly flowing the stem end material radially outward while chilling the molten ends, such as by application of pressure by a cold roller.

For useful engagement in a broad array of non-woven materials and foams employed in several common industries, the hooking members preferably have a height of 0.008 inch (0.2 millimeter) or less. Molded hooking members of J-shape or palm tree shape preferably have re-entrant tips disposed less than about 0.003 inch (0.008 millimeter) from the upper surface of the hooking members, as measured normal to the base, and a thickness of less than about 0.005 inch (0.13 millimeter).

According to one aspect of the invention, a fastening tape has a sheet-form base carrying an array of hooking members, each hooking member having a stem integrally molded with and extending from a side of the base, and a head overhanging the base in a common direction along the tape. The head extends from the stem to a distal, re-entrant tip to define an engageable crook. The hooking members each have a height of about 0.008 inch (0.2 millimeter) or less, as measured from the base, and the re-entrant tips are each disposed less than about 0.003 inch (0.08 millimeter) from an upper surface of their respective hooking members, as measured normal to the base.

In some embodiments the hooking members are of J-shape, preferably with stems having tapered pedestal profiles with front and rear edges defining an included angle ($\alpha$) of about 60 degrees.

In some other embodiments the hooking members are of palm tree shape, each having two re-entrant tips and defining two engageable crooks, preferably with stems having front and rear edges defining an included angle of about 24.5 degrees.

Preferably, the hooking members each have a thickness, as molded, of less than about 0.005 inch (0.13 millimeter).

According to another aspect of the invention, a wearable garment has a non-woven material broadly covering an outer surface thereof, and a piece of the featured fastening tape permanently attached to one region of the non-woven material and releasably engaging another portion of the non-woven material, with the hooking members of the fastening tape each directly engaging the non-woven material.

In various embodiments, the wearable garment is a medical gown, a face mask, or a diaper, for example.

In another aspect of the invention, a roll of moisture barrier construction wrap material has a length of the featured fastener tape permanently secured thereto. The wrap material may be a sheet of non-woven polypropylene, for example.

In another aspect of the invention, a releasable fastening essentially comprises a length of the featured fastener tape as a first half of the fastening, and an open cell foam as a second half of the fastening. The hooking members of the fastener tape are disposed within apertures of an open cell structure of the foam to engage reticulated portions of the foam in their crooks.

According to yet another aspect of the invention, a method of covering a structure is provided. The method includes providing a covering consisting essentially of a sheet of non-woven material and a length of the featured fastener tape permanently secured to the non-woven material in a first region thereof; wrapping the structure with the covering, such that a second region of the non-woven material overlaps the fastener tape in the first region; and engaging the hooking members of the fastener tape directly into the non-woven material to releasably secure the covering to itself.

In some applications, the non-woven material is polypropylene moisture barrier construction wrap material, and the structure is a wall surface.

According to another aspect of the invention, a method of securing a garment includes providing a garment with a non-woven material broadly covering an outer surface thereof, and a piece of the featured fastening tape permanently attached to one region of the non-woven material; overlapping a second region of the non-woven material with the fastener tape in the first region; and engaging the hooking members of the fastener tape directly into the non-woven material to releasably secure the non-woven material of the garment to itself.

The profile shapes of the hooking members shown in the illustrated embodiments, in combination with their small size, are particularly useful for engaging many fine-featured materials, as the wide bases of the hooking members resists vertical deflection of the hooks as they penetrate the mating material.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a side view of a first J-shaped hooking member.

FIG. 1A is an end view of the hooking member of FIG. 1.

FIG. 2 is a side view of a second J-shaped hooking member.

FIG. 2A is an end view of the hooking member of FIG. 2.

FIG. 3 is a side view of a palm tree shaped hooking member.

FIG. 3A is an end view of the hooking member of FIG. 3.

FIG. 4 is a side view of a mushroom-shaped hooking member.

FIG. 4A is an end view of the hooking member of FIG. 4.

Like reference symbols in the various drawings indicate like elements.

DETAILED DESCRIPTION

Figure 5:
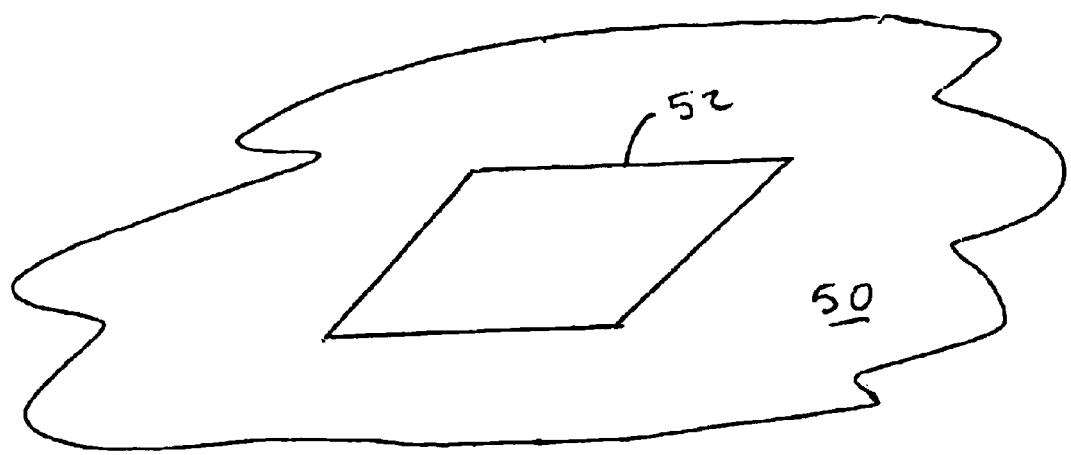
FIG. 5 is a perspective view of a fastener on a wearable garment (such as a diaper, face mask or medical gown) with a non-woven material broadly covering an outer surface, or a roll of moisture barrier construction wrap material.

The hooking member 10 of FIGS. 1 and 1A has a J-shaped profile and curved sides, such as may be molded in a cavity formed between two adjacent mold plates in a mold roll employed in the Fischer process, leaving a parting line 12 down the middle of the hook at the interface between the two mold plates. The pedestal stem portion defines a rather large included angle a of about 61.5 degrees between front and rear edges. The bead portion 16 has a re-entrant tip 18, meaning that it extends downward toward the base of the book to form a concave crook 20 for trapping features of a mating material. Tip 18 extends downward to a distance "d" of about 0.0028 inch (0.07 millimeter) from the most upper surface of the hooking member, and the entire booking member has an overall height "h", as measured normal to the base, of only about 0.0076 inch (0.19 millimeter).

The hooking member 22 of FIGS. 2 and 2A also has a J-shaped profile, but has flat sides as seen in FIG. 2A. Thus, its tip 18' extends completely across the hooking member, and the upper surface of its bead portion 16' presents a rather broad surface to the mating material. Stem portion 14' defines the same included angle a of about 61.5 degrees, top 18' also extends down to a distance "d" of about 0.0028 inch (0.07 millimeter), and hooking member 22 also has a height "h" of only about 0.0076 inch (0.19 millimeter).

The hooking member 24 of FIGS. 3 and 3A has a palm tree shaped profile, as seen in FIG. 3. As such, it has two bead portions 26 that extend from a common stem portion 28 to overhang the base in opposite directions, defining two discrete feature-trapping crooks 30. In this case, stem portion 28 defines an included angle $\alpha'$ of about 24.5 degrees between front and rear edges. Tips 32 also extend down to a distance "d" of about 0.0028 inch (0.07 millimeter), and hooking member 24 also has a height "h" of only about 0.0076 inch (0.19 millimeter).

The hooking member 34 of FIGS. 4 and 4A is a mushroom-type hooking member, having a molded stem portion 36 and an enlarged head portion 38. The stem portion is of square cross-section, each side having a nominal lateral dimension "t" of about 0.004 inch (0.1 millimeter), and was molded to have a total height of 0.133 inch (3.4 millimeters). After molding, the upper part of stem portion 36 was flame-heated and passed under a cold roll to cause the resin of the upper end of the stem portion to flow radially outward to form a generally circular disk-shaped head portion 38 having an overall dimension "D" of about 0.0092 inch (0.23 millimeter) and a vertical thickness "$d_1$" of only about 0.002 inch (0.05 millimeter). After this post-forming of head portion 38, hooking member 34 has a final overall height "$h_1$" of about 0.0105 inch (0.27 millimeter). In another embodiment (not shown), head portion 38 is of generally elliptical shape, having a major axis dimension of 0.0097 inch (0.25 millimeter) and a minor axis dimension of 0.0086 inch (0.22 millimeter).

Each of the hooks described above is useful for engaging many common surface materials, such as non-woven fabrics and open cell foams, and can be permanently bonded to garments and other products by ultrasonic or adhesive bonding. In one application, a non-woven medical gown, available as Medicom Non-Woven Gown REF 8012 blue from A.R. Medicom Inc. of Buffalo, N.Y., was provided with a patch of hook tape 52 having an array of hooking members 22 (as shown in FIGS. 2 and 2A). Engaging directly into the non-woven material of the medical gown (i.e., without any added loop material), the hook tape provided sufficient fastening strength to perform as a garment closure. As lightly pressed against the non-woven gown material by rolling a 4.5 pound roller topped with 1 kilogram of additional weight back and forth one time, in the direction of the hooks, across a one inch by two inch (25 millimeter by 50 millimeter) patch of hook tape, the hook tape exhibited a peel resistance of about 15 to 18 grams per inch (6 to 7 grams per centimeter) of width (as a three highest peak average), and a maximum shear resistance of 830 to 1085 grams per square inch (130 to 170 grams per square centimeter). Other medical applications for which this hook is suitable include engagement of face masks, surgery drapes, or bandages. These small hooking members are also useful in the direct engagement of many of the non-woven and other materials employed to broadly cover the outer surfaces of diapers.

However, these particularly small, strong hooking members are also useful in other industries. For example, we have found that in large arrays they provide sufficient engagement in common low pile, fine denier, non-woven polypropylene moisture barrier construction wrap material (e.g., such as is known under the trade names TYVEK and TYPAR) that they can be employed to secure such materials in place against wall surfaces instead of adhesive tape or staples. Such hooks can be provided on the surface to which the wrap is to be applied, or can be provided on one side of the wrap itself, such that the wrap can be wrapped about a structure and secured to itself. Other industrial packaging applications are envisioned, as are covers for vehicles and such.

In addition, these small hooking members are useful in the direct engagement of open cell foams, either of thermoset or thermoplastic materials. The head portions of the hooking members, particularly of the J-shaped and palm tree shaped hooking members, are small enough to fit within the apertures defined by the open cell structure of the foam to trap reticulated portions of the foam material in crooks of the hooks. Thus, these hooks can be used to advantage in many applications commonly employing such foams as filters (for air or liquid), padding (such as in fruit handling equipment), or insulation (automotive and industrial), to cite but a few examples. Suitable polyurethane foams include, for example, the HSS product of Lendell Manufacturing of St. Charles, Mich.

FIG. 5 illustrates a portion of a wearable garment 50 (such as a diaper, face mask or medical gown) with a non-woven material broadly covering its outer surface, and a piece of fastening tape 52 permanently attached to one region of the non-woven material. The fastening tape 52 can releasably engage another portion of the non-woven material, with the hooking members (10,22,24) of the fastening tape each directly engaging the non-woven material. Alternatively, the fastener tape 52 can be permanently secured to a roll of moisture barrier construction wrap material 50.

Figure 6:
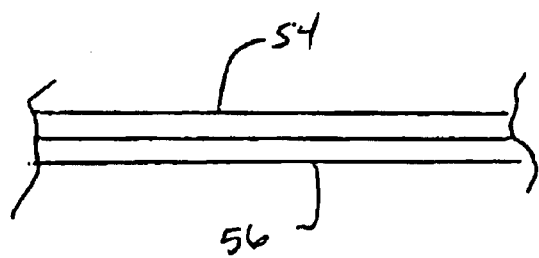
FIG. 6 illustrates a releasable fastening with a length of fastener tape as a first half of the fastening, and an open cell foam as a second half of the fastening.

FIG. 6 illustrates a releasable fastening with a length of fastener tape 54 as a first half of the fastening, and an open cell foam 56 as a second half of the fastening, with the hooking members of the fastener tape disposed within apertures of an open cell structure of the foam to engage reticulated portions of the foam in their crooks.

A number of embodiments of the invention have been described. Nevertheless, it will be understood that various modifications may be made without departing from the spirit and scope of the invention. Accordingly, other embodiments are within the scope of our invention.

What is claimed is:

1. A wearable garment with a non-woven material broadly covering an outer surface thereof, and a piece of fastening tape permanently attached to one region of the non-woven material and releasably engaging another portion of the non-woven material,
the fastening tape comprising a sheet-form base carrying an array of hooking members, each hooking member having a stem integrally molded with and extending from a side of the base, and a head overhanging the base in a common direction along the tape, the head extending from the stem to a distal, re-entrant tip to define an engageable crook;
wherein the hooking members each have a height of about 0.008 inch or less, as measured from the base, and the re-entrant tips are each disposed less than about 0.003 inch from an upper surface of their respective hooking members, as measured normal to the base;
with the hooking members of the fastening tape each directly engaging the non-woven material.

2. The wearable garment of claim 1 wherein the hooking members are of J-shape.

3. The wearable garment of claim 2 wherein the stems of the hooking members have tapered pedestal profiles with front and rear edges defining an included angle of about 60 degrees.

4. The wearable garment of claim 1 wherein the hooking members are of palm tree shape, each having two re-entrant tips and defining two engageable crooks.

5. The wearable garment of claim 4 wherein the stems of the hooking members have front and rear edges defining an included angle of about 24.5 degrees.

6. The wearable garment of claim 1 wherein the hooking members each have a thickness, as molded, of less than about 0.005 inch.

7. The wearable garment of claim 1 wherein the fastening tape is constructed such that a one inch by two inch patch of the fastening tape exhibits a maximum shear resistance of 830 to 1085 grams per square inch, as lightly pressed against the non-woven material by rolling a 4.5 pound roller topped with 1 kilogram of additional weight back and forth one time.

8. The wearable garment of claim 1 comprising a medical gown.

9. The wearable garment of claim 1 comprising a face mask.

10. The wearable garment of claim 1 comprising a diaper.

11. The wearable garment of claim 1 wherein the heads of the hooking members are of molded shape.

12. The wearable garment of claim 1 wherein the stems of the hooking members have flat sides.

13. The wearable garment of claim 1 wherein the hooking members comprise mushroom-type hooking members, each having a molded stem portion and an enlarged head portion.

14. The wearable garment of claim 13 wherein the stem portions are of square cross-section.

15. The wearable garment of claim 1 wherein the fastening tape is constructed such that a one inch by two inch patch of the fastening tape exhibits a peel resistance of about 15 to 18 grams per inch of width, as lightly pressed against the non-woven material by rolling a 4.5 pound roller topped with 1 kilogram of additional weight back and forth one time, as a three highest peak average.

16. A roll of moisture barrier construction wrap material having a length of fastener tape permanently secured thereto, the fastener tape comprising
a sheet-form base carrying an array of hooking members, each hooking member having a stem integrally molded with and extending from a side of the base, and a head overhanging the base in a common direction along the tape, the head extending from the stem to a distal, re-entrant tip to define an engageable crook; wherein
the hooking members each have a height of about 0.008 inch or less, as measured from the base; and the re-entrant tips are each disposed less than about 0.003 inch from an upper surface of their respective hooking members, as measured normal to the base.

17. The roll of moisture barrier construction wrap material of claim 16, wherein the wrap material comprises a sheet of non-woven polypropylene.

18. The roll of moisture barrier construction wrap material of claim 16 wherein the stems of the hooking members have flat sides.

19. The roll of moisture barrier construction wrap material of claim 16 wherein the hooking members comprise mushroom-type hooking members, each having a molded stem portion and an enlarged head portion.

20. The roll of moisture barrier construction wrap material of claim 19 wherein the stem portions are of square cross-section.

21. The roll of moisture barrier construction wrap material of claim 16 wherein the fastener tape is constructed such that a one inch by two inch patch of the fastener tape exhibits a peel resistance of about 15 to 18 grams per inch of width, as lightly pressed against the non-woven material by rolling a 4.5 pound roller topped with 1 kilogram of additional weight back and forth one time, as a three highest peak average.

22. The roll of moisture barrier construction wrap material of claim 16 wherein the fastener tape is constructed such that a one inch by two inch patch of the fastener tape exhibits a maximum shear resistance of 830 to 1085 grams per square inch, as lightly pressed against the non-woven material by rolling a 4.5 pound roller topped with 1 kilogram of additional weight back and forth one time.

23. The roll of moisture barrier construction wrap material of claim 16 wherein the hooking members are of J-shape.

24. The roll of moisture barrier construction wrap material of claim 23 wherein the stems of the hooking members have tapered pedestal profiles with front and rear edges defining an included angle of about 60 degrees.

25. The roll of moisture barrier construction wrap material of claim 16 wherein the hooking members are of palm tree shape, each having two re-entrant tips and defining two engageable crooks.

26. The roll of moisture barrier construction wrap material of claim 25 wherein the stems of the hooking members have front and rear edges defining an included angle of about 24.5 degrees.

27. The roll of moisture barrier construction wrap material of claim 16 wherein the hooking members each have a thickness, as molded, of less than about 0.005 inch.

28. The roll of moisture barrier construction wrap material of claim 16 wherein the heads of the hooking members are of molded shape.

29. A releasable fastening comprising
a length of fastener tape as a first half of the fastening, the fastener tape comprising a sheet-form base carrying an array of hooking members, each hooking member having a stem integrally molded with and extending from a side of the base, and a head overhanging the base in a common direction along the tape, the head extending from the stem to a distal, re-entrant tip to define an engageable crook;
wherein the hooking members each have a height of about 0.008 inch or less, as measured from the base, and the re-entrant tips are each disposed less than about 0.003 inch from an upper surface of their respective hooking members, as measured normal to the base; and
an open cell foam as a second half of the fastening;
wherein the hooking members of the fastener tape are disposed within apertures of an open cell structure of the foam to engage reticulated portions of the foam in their crooks.

30. The releasable fastening of claim 29 wherein the hooking members comprise mushroom-type hooking members, each having a molded stem portion and an enlarged head portion.

31. The releasable fastening of claim 30 wherein the stem portions are of square cross-section.

32. The releasable fastening of claim 29 wherein the fastener tape is constructed such that a one inch by two inch patch of the fastener tape exhibits a peel resistance of about 15 to 18 grams per inch of width, as lightly pressed against the non-woven material by rolling a 4.5 pound roller topped with 1 kilogram of additional weight back and forth one time, as a three highest peak average.

33. The releasable fastening of claim 29 wherein the fastener tape is constructed such that a one inch by two inch patch of the fastener tape exhibits a maximum shear resistance of 830 to 1085 grams per square inch, as lightly pressed against the non-woven material by rolling a 4.5 pound roller topped with 1 kilogram of additional weight back and forth one time.

34. The releasable fastening of claim 29 wherein the hooking members are of J-shape.

35. The releasable fastening of claim 34 wherein the stems of the hooking members have tapered pedestal profiles with front and rear edges defining an included angle of about 60 degrees.

36. The releasable fastening of claim 29 wherein the hooking members are of palm tree shape, each having two re-entrant tips and defining two engageable crooks.

37. The releasable fastening of claim 36 wherein the stems of the hooking members have front and rear edges defining an included angle of about 24.5 degrees.

38. The releasable fastening of claim 29 wherein the hooking members each have a thickness, as molded, of less than about 0.005 inch.

39. The releasable fastening of claim 29 wherein the heads of the hooking members are of molded shape.

40. The releasable fastening of claim 29 wherein the stems of the hooking members have flat sides.

41. A method of covering a structure, the method comprising providing a covering consisting essentially of
a sheet of non-woven material; and
a length of fastener tape permanently secured to the non-woven material in a first region thereof, the fastener tape comprising a sheet-form base carrying an array of hooking members, each hooking member having a stem integrally molded with and extending from a side of the base, and a head overhanging the base in a common direction along the tape, the head extending from the stem to a distal, re-entrant tip to define an engageable crook, the hooking members each having a height of about 0.008 inch or less, as measured from the base, and the re-entrant tips each disposed less than about 0.003 inch from an upper surface of their respective hooking members, as measured normal to the base;
wrapping the structure with the covering, such that a second region of the non-woven material overlaps the fastener tape in the first region; and
engaging the hooking members of the fastener tape directly into the non-woven material to releasably secure the covering to itself.

42. The method of claim 41 wherein the non-woven material is polypropylene moisture barrier construction wrap material, and wherein the structure is a wall surface.

43. The method of claim 41 wherein the fastener tape is constructed such that a one inch by two inch patch of the fastener tape exhibits a peel resistance of about 15 to 18 grams per inch of width, as lightly pressed against the non-woven material by rolling a 4.5 pound roller topped with 1 kilogram of additional weight back and forth one time, as a three highest peak average.

44. The method of claim 41 wherein the fastener tape is constructed such that a one inch by two inch patch of the fastener tape exhibits a maximum shear resistance of 830 to 1085 grams per square inch, as lightly pressed against the non-woven material by rolling a 4.5 pound roller topped with 1 kilogram of additional weight back and forth one time.

45. The method of claim 41 wherein the hooking members are of J-shape.

46. The method of claim 45 wherein the stems of the hooking members have tapered pedestal profiles with front and rear edges defining an included angle of about 60 degrees.

47. The method of claim 41 wherein the hooking members are of palm tree shape, each having two re-entrant tips and defining two engageable crooks.

48. The method of claim 47 wherein the stems of the hooking members have front and rear edges defining an included angle of about 24.5 degrees.

49. The method of claim 41 wherein the hooking members each have a thickness, as molded, of less than about 0.005 inch.

50. The method of claim 41 wherein the heads of the hooking members are of molded shape.

51. The method of claim 41 wherein the stems of the hooking members have flat sides.

52. The method of claim 41 wherein the hooking members comprise mushroom-type hooking members, each having a molded stem portion and an enlarged head portion.

53. The method of claim 52 wherein the stem portions are of square cross-section.

54. A method of securing a garment, the method comprising providing a garment with a non-woven material broadly covering an outer surface thereof, and a piece of fastener tape permanently attached to one region of the non-woven material, the fastener tape comprising a sheet-form base carrying an array of hooking members, each hooking member having a stem integrally molded with and extending from a side of the base, and a head overhanging the base in a common direction along the tape, the head extending from the stem to a distal, re-entrant tip to define an engageable crook, the hooking members each having a height of about 0.008 inch or less, as measured from the base, and the re-entrant tips each disposed less than about 0.003 inch from an upper surface of their respective hooking members, as measured normal to the base;

overlapping a second region of the non-woven material with the fastener tape in the first region; and engaging the hooking members of the fastener tape directly into the non-woven material to releasably secure the non-woven material of the garment to itself.

55. The method of claim 54 wherein the fastener tape is constructed such that a one inch by two inch patch of the fastener tape exhibits a maximum shear resistance of 830 to 1085 grams per square inch, as lightly pressed against the non-woven material by rolling a 4.5 pound roller topped with 1 kilogram of additional weight back and forth one time.

56. The method of claim 54 wherein the hooking members are of J-shape.

57. The method of claim 56 wherein the stems of the hooking members have tapered pedestal profiles with front and rear edges defining an included angle of about 60 degrees.

58. The method of claim 54 wherein the hooking members are of palm tree shape, each having two re-entrant tips and defining two engageable crooks.

59. The method of claim 58 wherein the stems of the hooking members have front and rear edges defining an included angle of about 24.5 degrees.

60. The method of claim 54 wherein the hooking members each have a thickness, as molded, of less than about 0.005 inch.

61. The method of claim 54 wherein the heads of the hooking members are of molded shape.

62. The method of claim 54 wherein the stems of the hooking members have flat sides.

63. The method of claim 54 wherein the hooking members comprise mushroom-type hooking members, each having a molded stem portion and an enlarged head portion.

64. The method of claim 63 wherein the stem portions are of square cross-section.

65. The method of claim 54 wherein the fastener tape is constructed such that a one inch by two inch patch of the fastener tape exhibits a peel resistance of about 15 to 18 grams per inch of width, as lightly pressed against the non-woven material by rolling a 4.5 pound roller topped with 1 kilogram of additional weight back and forth one time, as a three highest peak average.

* * * * *